United States Patent [19]
Janssen et al.

[11] 3,989,707
[45] Nov. 2, 1976

[54] BENZIMIDAZOLINONE DERIVATIVES

[75] Inventors: Paul Adriaan Jan Janssen; Albert H. M. Th. Van Heertum, both of Vosselaar; Jan Vandenberk, Beerse; Marcel J. M. C. Van der Aa, Vosselaar, Belgium

[73] Assignee: Janssen Pharmaceutica N.V., Beerse, Belgium

[22] Filed: June 21, 1974

[21] Appl. No.: 481,594

[52] U.S. Cl. .................. 260/293.6; 260/293.76; 260/293.86; 424/267
[51] Int. Cl.$^2$ .................................. C07D 401/04
[58] Field of Search ............................ 260/293.6

[56] References Cited
UNITED STATES PATENTS

| | | | |
|---|---|---|---|
| 3,161,645 | 12/1964 | Janssen | 260/293.4 |
| 3,196,157 | 7/1965 | Janssen | 260/294 |
| 3,338,916 | 8/1967 | Hunziker | 260/309.2 |
| 3,799,932 | 3/1974 | Yamamoto et al. | 260/293.6 |
| 3,840,529 | 10/1974 | Maruyama et al. | 260/240 R |

*Primary Examiner*—G. Thomas Todd
*Attorney, Agent, or Firm*—Salvatore R. Conte

[57] ABSTRACT

Novel benzimidazolinone derivatives and therapeutically acceptable acid addition salts thereof, said compounds being useful as long acting neuroleptic agents.

6 Claims, No Drawings

BENZIMIDAZOLINONE DERIVATIVES

BACKGROUND OF THE INVENTION

Among other differences the compounds of this invention differ from those of the prior art by the presence of substituents on the aromatic part of the benzimidazolinone group. Such prior art compounds are described in U.S. Pat. No. 3,196,157.

DESCRIPTION OF THE INVENTION

This invention relates to a new series of organic compounds, more particularly to novel benzimidazolinone derivatives having the formula:

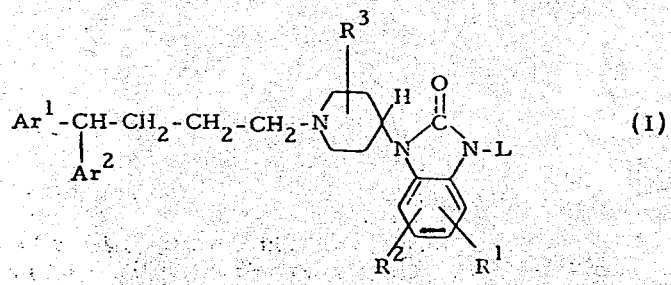

and the therapeutically acceptable acid addition salts thereof, wherein:

$Ar^1$ and $Ar^2$ are each a member independently selected from the group consisting of phenyl, halophenyl and trifluoromethylphenyl;

$R^1$ is a member selected from the group consisting of halo, loweralkyl and trifluoromethyl;

$R^2$ is a member selected from the group consisting of hydrogen, halo, loweralkyl and trifluoromethyl;

$R^3$ is a member selected from the group consisting of hydrogen and methyl, on the understanding that, when said $R^3$ is methyl, then said $R^3$ is in the 2- or 3-position of the piperidine-nucleus; and L is a member selected from the group consisting of hydrogen, loweralkyl, loweralkyloxycarbonyl-loweralkyl, loweralkylcarbonyl-loweralkyl, and phenyl-loweralkyl.

As used herein "loweralkyl" refers to a straight or branched hydrocarbon chain having from 1 to 5 carbon atoms, such as, for example, methyl, ethyl, propyl, isopropyl, butyl and the like alkyls. The term "halo" is generic to halogens of atomic weight less than 127, i.e. fluoro, chloro, bromo and iodo.

The compounds of this invention may be converted to their therapeutically useful acid addition salts by treatment with an appropriate acid, such as, for example, an inorganic acid, such as hydrohalic acid, e.g. hydrochloric, hydrobromic and the like, and sulfuric acid, nitric acid, phosphoric acid and the like; or an organic acid, such as, for example, acetic, propionic, glycolic, lactic, pyruvic, malonic, succinic, maleic, fumaric, malic, tartaric, citric, benzoic, cinnamic, mandelic, methanesulfonic, ethanesulfonic, benzenesulfonic, p-toluenesulfonic, cyclohexanesulfamic, salicylic, p-aminosalicylic and the like acids.

Conversely the salt form can be converted by treatment with alkali into the free base form.

Moreover, the compounds of formula (I) are able to form solvates with water and non-aqueous solvents such as, for example, alcohols, e.g. 2-propanol. Such solvates are naturally intended to be within the scope of this invention.

The compounds of formula (I) are conveniently prepared by reacting a reactive ester of formula (II) wherein $Ar^1$ and $Ar^2$ are as previously defined and X is a reactive ester function derived from the corresponding alcohol, such as, for example, halo, mesylate, tosylate and the like, preferably halo, with an appropriate piperidine derivative of formula (III) wherein $R^1$, $R^2$, $R^3$ and L are as previously defined.

Said reaction is preferably carried out under reflux conditions in an appropriate organic solvent, such as, for example, a lower alcohol, e.g. methanol, ethanol, propanol, n-butanol and the like alcohols; an aromatic hydrocarbon, e.g. benzene, toluene, xylene, and the like; a ketone, e.g., 4-methyl-2-pentanone; an ether, e.g. dioxane, diethyl ether and the like; dimethylformamide (DMF); nitrobenzene; and the like. The addition of an appropriate base such as, for example, an alkali metal carbonate or bicarbonate, may be utilized to pick up the acid that is liberated during the course of the reaction. A small amount of an appropriate iodide, e.g. sodium or potassium iodide, may be added as a reaction promotor. The thus-obtained compounds (I) may be further purified by generally known purification procedures.

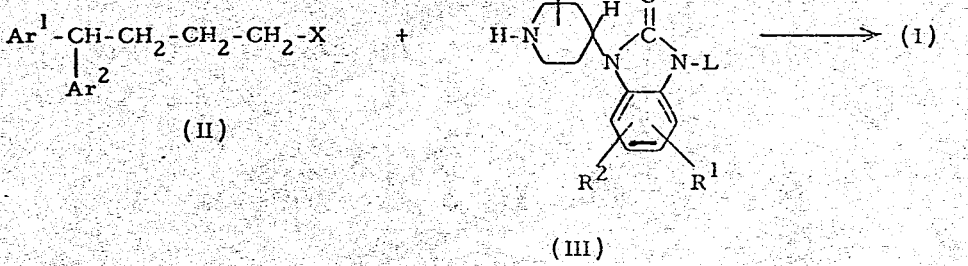

The compounds of formula (I) wherein L is loweralkyl, loweralkylcarbonyl-loweralkyl, loweralkyloxycarbonyl-loweralkyl or phenyl-loweralkyl (I-b) may alternatively be prepared starting from a compouund of formula (I) wherein L is hydrogen (I-a) by introducing said L by known alkylation methods, for example, by reaction (I-a) with an appropriate reactive ester XL (IV) wherein X is as previously defined and L is loweralkyl, loweralkylcarbonyl-loweralkyl, loweralkyloxycarbonyl-loweralkyl or phenyl-loweralkyl, by art known methods.

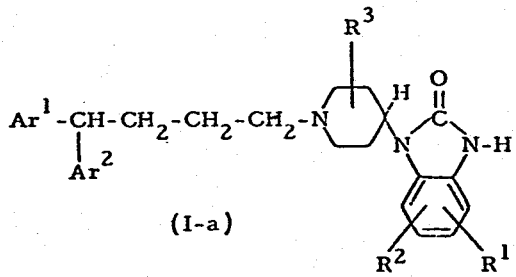

(I-a)         +         XL         ⟶         (I-b)

(IV)

The compounds of formula (I) wherein L is a loweralkyloxycarbonyl-ethyl radical (I-c) are conveniently obtained by reacting (I-a) with a loweralkyl 2-propenoate of formula (V). Said condensation reaction is carried out in an appropriate reaction inert organic solvent, such as, for example, an aromatic hydrocarbon, such as benzene, toluene, xylene and the like; an ether such as dimethyl ether, diethyl ether, diisopropylether, tetrahydrofuran, dioxane and the like; or in a halogenated hydrocarbon, such as chloroform, methylene chloride and the like. The reaction is preferably conducted in the presence of an appropriate quaternary aminiumhydroxide, such as N,N,N-trimethylbenzenemethanaminium hydroxide.

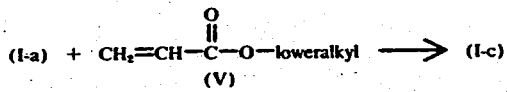

Compounds of formula (I) wherein L stands for loweralkylcarbonylmethyl (I-d) may be prepared alternatively by reacting (I-a) with a reactive ester of formula (VI) wherein X is as previously defined and n is an integer from 1 to 4 inclusive, followed by treatment of the thus-obtained compound of formula (VII) with alkali whereby the ketone derivative of formula (I-d) is obtained. The foregoing reaction sequence is illustrated in the following schematic representation:

(I-a)    +    $X\text{-}CH_2\text{-}C{\equiv}C\text{-}C_{n-1}H_{2n-1}$    ⟶

(VI)

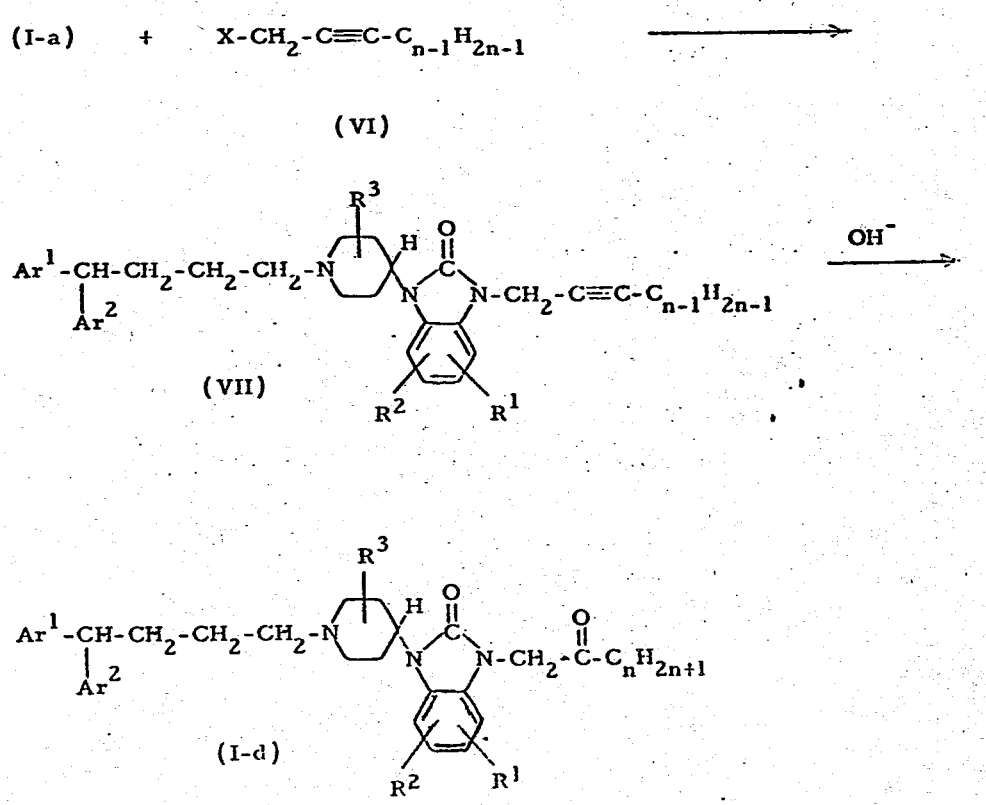

The intermediates of formula (II) are generally known and may be obtained by methods known in the art.

The intermediates of formula (III), a number of which are known compounds, may be prepared according to known methodologies, such as for example described in U.S. Pat. No. 3,161,645 and in U.S. Pat. appln. Ser. No. 417.702.

The 1,3-dihydro-1-(4-piperidinyl)-2H-benzimidazol-2-ones of formula (III) wherein L is hydrogen (III-a) may for example be prepared as follows:

A 4-piperidone (VIII) having an appropriate protecting group, such as loweralkoxycarbonyl or phenylmethyl on the piperidine nitrogen, is reacted with hydroxylamine whereby the corresponding oxime (IX) is obtained, which by catalytic hydrogenation, for example on Raney-nickel catalyst, yields the 4-aminopiperidine derivative of formula (X). The compound of formula (X) is then reacted with an appropriate o-nitro-halobenzene of formula (XI) in a suitable organic solvent, e.g. cyclohexanol, in the presence of an acid acceptor, such as, for example, a metal carbonate or bicarbonate. The reaction may be promoted by the addition of a small amount of an iodide, preferably an alkali or earth alkali iodide. The nitro-function of the resulting 4-anilinopiperidine (XII) is then reduced to an amino function for example by catalytic hydrogenation, e.g. over Raney-nickel catalyst. The resulting (XIII) is then subjected to ring closure by heating with an appropriate cyclizing agent, such as, urea, potassium isocyanate, phosgene and the like. The corresponding intermediates of formula (III-a) are obtained after removal of the protecting group of (XIV) by conventional means, such as, catalytic debenzylation, or alkaline hydrolysis when the protecting group is loweralkoxycarbonyl. The foregoing reactions are illustrated in the following scheme, wherein loweralkoxycarbonyl stands for the protecting group:

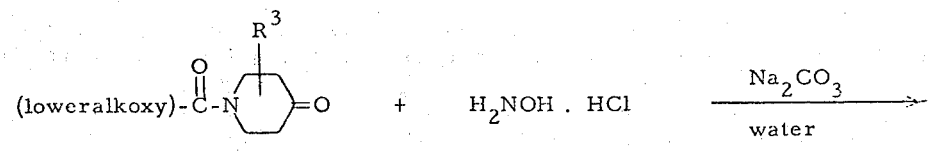

(VIII)

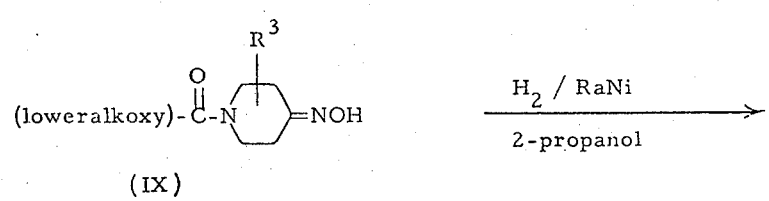

(IX)

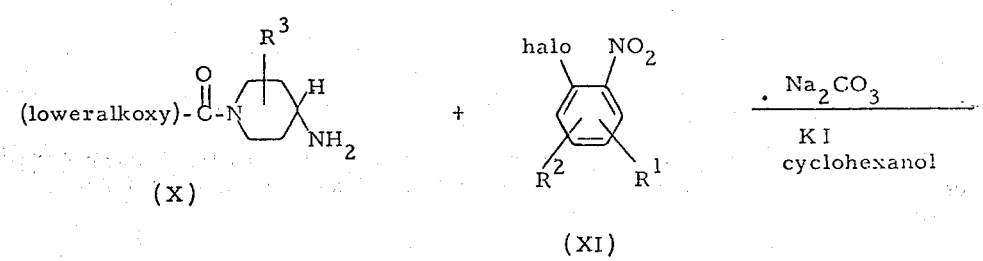

(X)                          (XI)

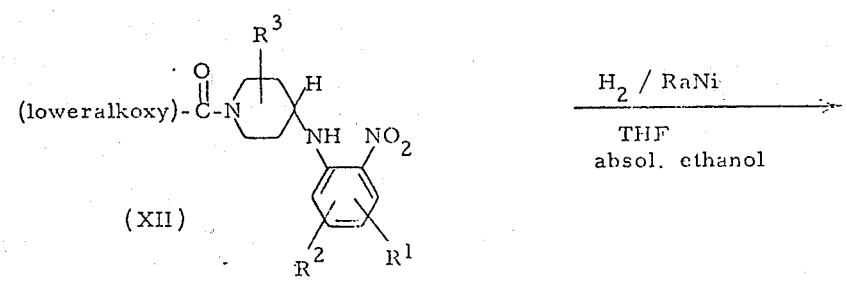

(XII)

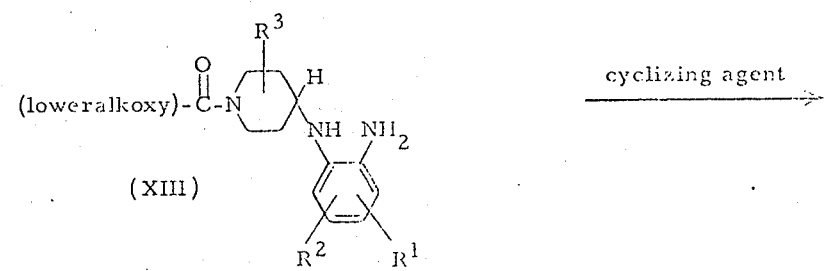

(XIII)

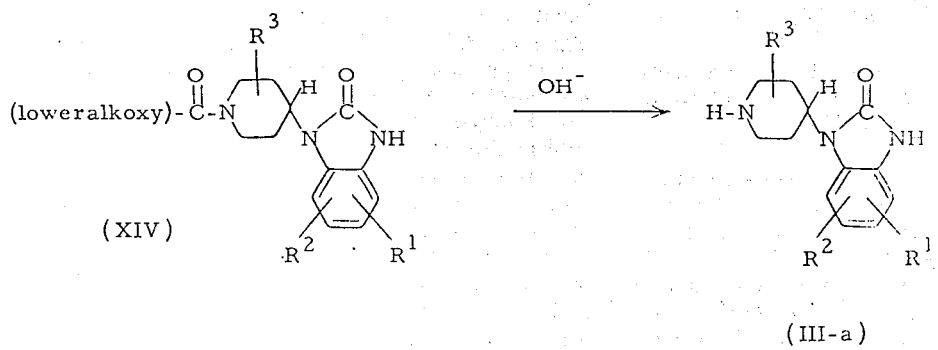

An alternative method for the preparation of the 4-piperidinamine of formula (X) consists in reacting (VIII) with benzylamine (XV) in an appropriate solvent, e.g., a lower alkanol, such as methanol, in the presence of an appropriate strong acid such as 4-methylbenzenesulfonic acid, followed by catalytic hydrogenation using for example, palladium-on-charcoal catalyst. The foregoing procedure is illustrated as follows:

carbonyl-loweralkyl or phenyl-loweralkyl (III-b), are conveniently prepared by introduction of said L into a compound of formula (XIV) to obtain (XVI) wherein L has the same meaning as heretobefore defined for (III-b), and thereafter removing the protecting group by conventional methods. The introduction of L into (XIV) may be performed by known methods as described hereinbefore for the introduction of said substitu-

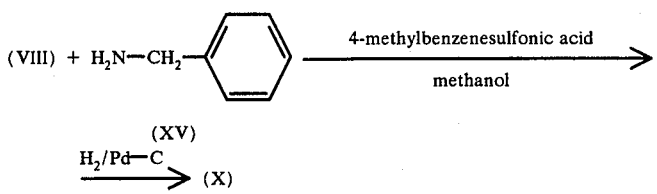

The intermediates of formula (III) wherein L is loweralkyl, loweralkyloxycarbonyl-loweralkyl, loweralkyl- ent in (I-a). The foregoing procedure may be schematically represented as follows:

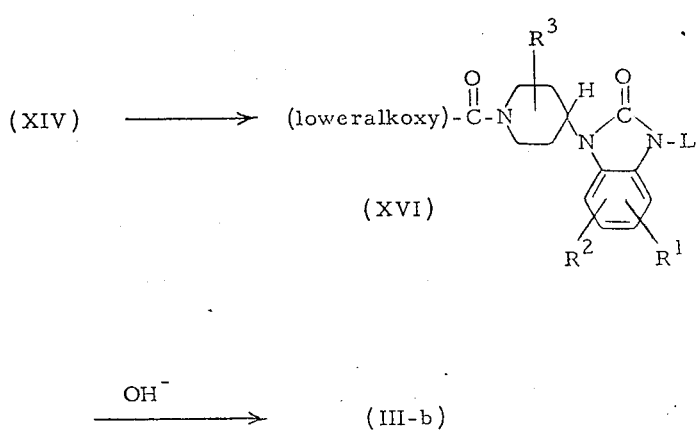

It is understood that in the foregoing synthetic routes the loweralkoxycarbonyl group on the piperidine nitrogen may be replaced by another appropriate protecting group, such as benzyl, in which case the corresponding compounds (III) are obtained after removal of said protecting group by conventional methods such as catalytic debenzylation.

It is believed that the intermediates of formula (III) wherein $R^1$ is a trifluoromethyl group, and $R^2$, $R^3$ and L have the same meaning as in formula (I) are novel and as useful intermediates herein they constitute an additional feature of this invention.

The piperidinone derivatives of formula (VIII) wherein $R^3$ has the meaning of hydrogen (VIII-a) or a methyl group in the 3-position of the piperidine-ring (VIII-b) are generally known and may be prepared by methods known in the art. Those precursors of formula (VIII) wherein $R^3$ is a methyl group in the 2-position of the piperidine-ring may be prepared, for example, by the following procedure.

A loweralkyl 3-[(phenylmethyl)amino]butanoate of formula (XVII) is reacted with a loweralkylpropenoate of formula (XVIII) in an appropriate solvent, such as a lower alkanol, e.g., ethanol, under reflux for several hours. After the reaction is completed, the solvent is evaporated and there is obtained a mixture of a loweralkyl N-[2-(loweralkoxycarbonyl)-1-methylethyl]-N-(phenylmethyl)-β-alanine (XIX) and a loweralkyl N-[2-(loweralkoxycarbonyl)ethyl]-N-(phenylmethyl)-β-alanine (XX).

In order to separate the first compound from the latter, the residue is treated with a loweralkyl chloroformate in an appropriate organic solvent, for example, a halogenated hydrocarbon, such as, dichloromethane, trichloromethane, tetrachloromethane and the like, in the presence of an appropriate base such as an alkali or earth alkali metal carbonate or bicarbonate.

Under these conditions the phenylmethyl group of (XX) is replaced by a loweralkoxycarbonyl group, resulting in a compound of formula (XXI), while (XIX) remains unchanged. Since (XIX) is more basic than (XXI) the first compound may be isolated from the mixture by extraction with a diluted solution of an acid, e.g., hydrochloric acid, whereafter the free base form of (XIX) is set free by treatment with alkali.

The phenylmethyl function of (XIX) is then removed by catalytic hydrogenation using palladium-on-charcoal catalyst and the thus-obtained compound (XXII) is converted into the corresponding N-loweralkoxycarbonyl derivative of formula (XXIII) in the usual manner, by treatment with a loweralkyl chloroformate in a suitable solvent, e.g., trichloromethane, in the presence of an acid acceptor, such as, for example, N,N-diethylethanamine.

The piperidinone derivative of formula (XXIV) is then obtained by treating (XXIII) with an appropriate strong base, such as sodium methanolate, for example in an aromatic hydrocarbon, such as benzene, methylbenzene, dimethylbenzene and the like. The compound (XXIV) is then heated in an acidic medium, e.g., a solution of ethanedioic acid in water, whereupon the desired intermediate of formula (VIII-c) is obtained.

The foregoing procedure is illustrated in the following schematic representation:

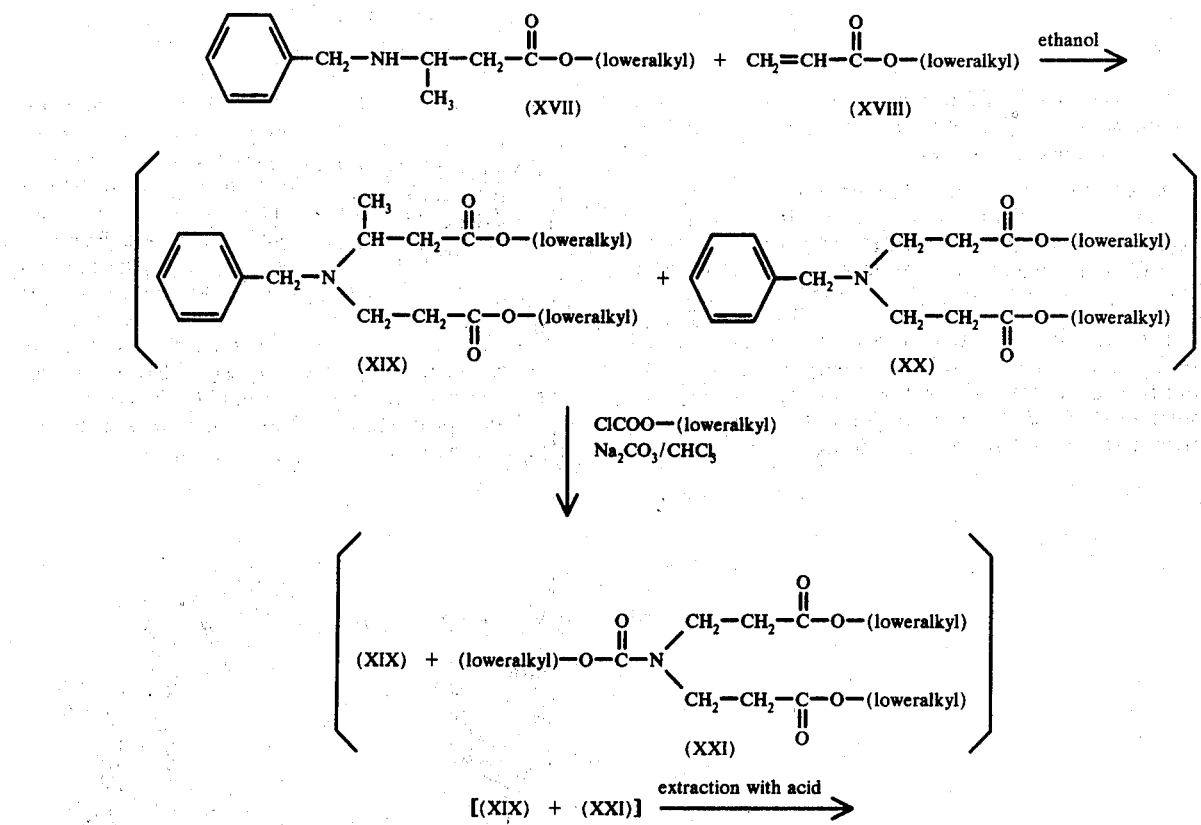

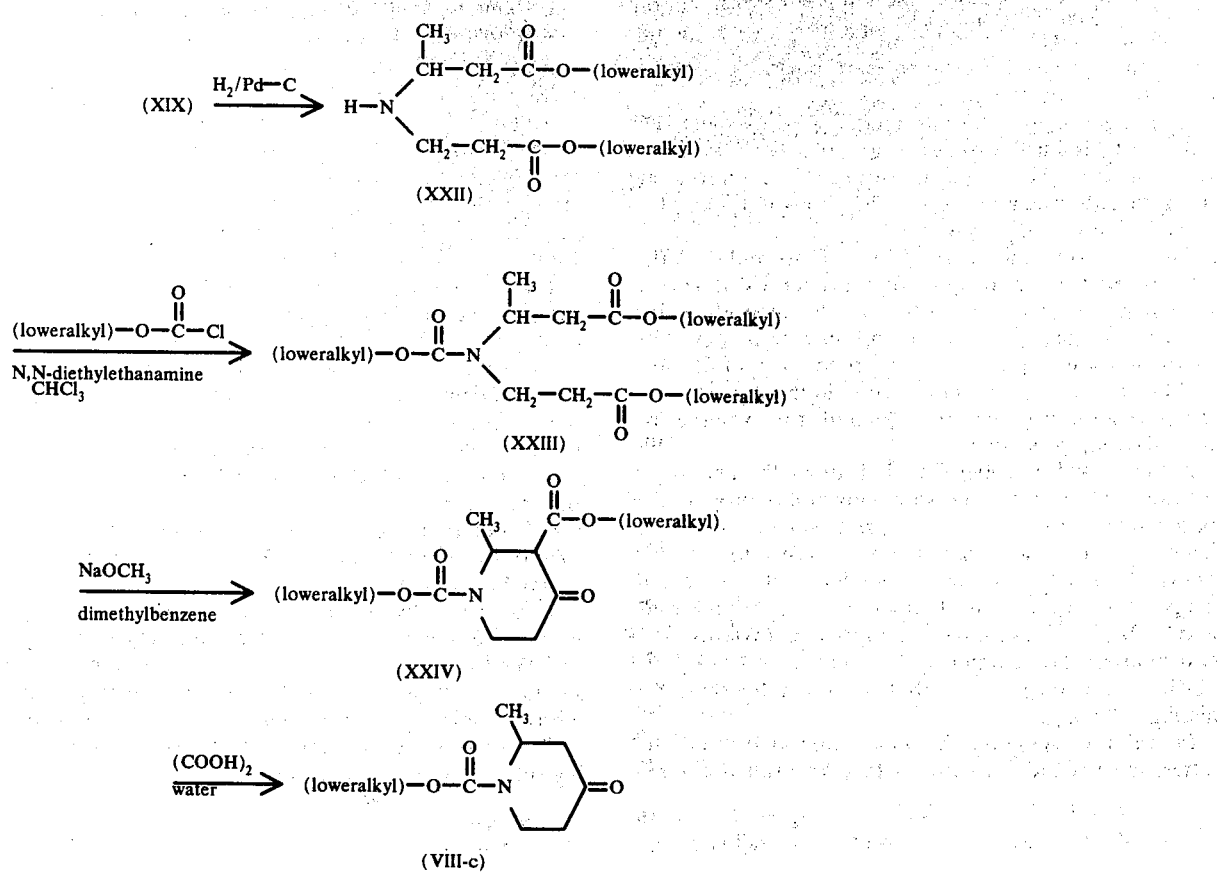

The compounds of formula (I) are potent neuroleptic agents with a very long duration of action. Such activity was determined as follows:

All potent and specific neuroleptic drugs are known to inhibit emesis induced by apomorphine in dogs. The method used is described previously by P. A. J. Janssen and C. J. E. Niemegeers in: Arzneim.-Forsch. (Drug Res.), 9, 765–767 (1959).

The compounds listed below were administered orally to at least a group of three beagle dogs at a standard dose of 0.04 mg/kg body weight. The animals were challenged at different time intervals thereafter with a standard dose of 0.31 mg/kg of apomorphine, i.e. after 4 hours, 16 hours, 24 hours, and further every day till vomiting occurred in all treated dogs.

The table below gives the duration of action of a single oral dose of 0.04 mg/kg of the drug under investigation. The first compound in the table is the reference drug 1-[4,4-bis(4-fluorophenyl)butyl]-4-piperidinyl-1,3-dihydro-2H-benzimidazol-2-one, described in U.S. Pat. No. 3,196,157 and generically designated as pimozide.

It is understood that the compounds shown in the table are not listed for the purpose of limiting the invention thereto, but only to exemplify the outstanding neuroleptic properties of all the compounds within the scope of formula (I).

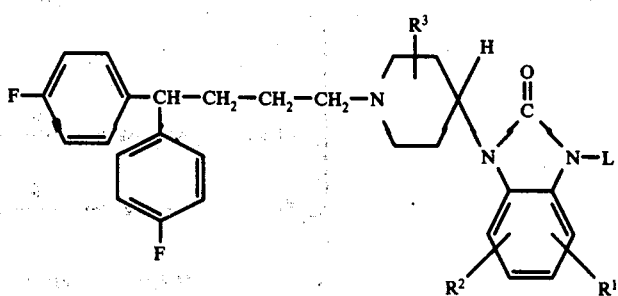

| L | $R^1, R^2$ | $R^3$ | Duration of action of a single oral dose of 0.04 mg/kg |
|---|---|---|---|
| H | H | H | 16 hours |
| H | 5-Cl | H | 216 hours |
| H | 5-F | H | 48 hours |
| H | 5-Me | H | 24 to 32 hours |
| H | 6-Cl | H | 48 hours |
| H | 5,6-(Cl)$_2$ | H | 120 hours |
| H | 5-CF$_3$, 6-Cl | H | 24 to 32 hours |
| H | 5-Cl | 3-Me | 96 hours |
| H | 5-Br | H | 168 hours |
| H | 5-Cl | 2-Me | 24 to 32 hours |
| —CH$_2$—CH$_2$—COOMe | 5-Cl | H | 192 hours |
| CH$_3$ | 5-Cl | H | 48 hours |

As is apparent from the data in the table, the compounds of the present invention show a much longer duration of action than the reference drug pimozide, when given at the same dose. Such an improvement of neuroleptic activity as a result of introducing the substituents $R^1$ and $R^2$ in the benzimidazolinone moiety was completely unexpected.

It is evident that the finding of neuroleptic agents with a very long duration of action is a highly desirable objective since they permit patients to be treated with less applications of drugs. This is especially important when treatment over a longer time is needed.

From formula (I) it is evident that several of the compounds of this invention have one or more asymmetric carbon atoms in their structure, and consequently exist under different stereochemical optical isomeric forms.

More particularly when $R^3$ is a methyl group, then the carbon atom to which $R^3$ is attached and the carbon atom in the 4-position of the piperidine nucleus are asymmetric. When $Ar^1$ and $Ar^2$ represent different aromatic groups, then the carbon atom to which they are attached is also asymmetric.

Stereochemical optical isomeric forms of the compounds of formula (I) are intended to be within the scope of this invention.

The following examples are intended to illustrate, and not to limit the scope of the present invention. Unless otherwise stated, all parts are by weight.

A. PREPARATION OF FORMULA (III) PRECURSORS

EXAMPLE I

A mixture of 43 parts of ethyl 4-amino-1-piperidinecarboxylate, 67.6 parts of 4-chloro-α,α,α-trifluoro-3-nitrotoluene, 32 parts of sodium carbonate, 0.2 parts of potassium iodide and 175 parts of cyclohexanol is stirred and heated at 160° C for 48 hours with water-separator. The reaction mixture is cooled and to the resulting solid mass are added toluene and water. The layers are separated and the organic layer is washed with water, dried, filtered and evaporated. The residue is crystallized from diisopropylether. The product is filtered off and dried, yielding ethyl 4-(α,α,α-trifluoro-2-nitro-p-toluidino)-1-piperidinecarboxylate; mp. 126.6° C.

A mixture of 70 parts of ethyl 4-(α,α,α-trifluoro-2-nitro-p-toluidino)-1-piperidinecarboxylate, 120 parts of ethanol and 270 parts of tetrahydrofuran is hydrogenated at normal pressure and at 40°–45° C with 20 parts of raney-nickel catalyst. After the calculated amount of hydrogen is taken up, the catalyst is filtered off over hyflo and the filtrate is evaporated. The residue is triturated in 2,2'-oxybispropane. The product is filtered off and dried, yielding 58 parts of ethyl 4-[2-amino-4-(trifluoromethyl)phenylamino]-1-piperidinecarboxylate.

56.27 parts of ethyl 4-[2-amino-4-(trifluoromethyl)phenylamino]-1-piperidinecarboxylate and 15.6 parts of urea are mixed thoroughly in a mortar. The mixture is stirred and heated on an oil-bath at 170°–180° C for 3 hours. The reaction mixture is cooled to 100° C and the product is extracted with methylbenzene. The extract is washed with water, dried, filtered and evaporated. The residue is crystallized from 2,2'-oxybispropane. The product is filtered off and dried, yielding ethyl 4-[1,3-dihydro-2-oxo-5-(trifluoromethyl)-2H-benzimidazol-1-yl]-1-piperidinecarboxylate.

A mixture of 26 parts of ethyl 4-[1,3-dihydro-2-oxo-5-(trifluoromethyl)-2H-benzimidazol-1-yl]-1-piperidinecarboxylate, 30 parts of potassium hydroxide, 176 parts of 2-propanol and 4 parts of water is stirred and refluxed for 20 hours. The reaction mixture is evaporated. The residue is dissolved in water, acidified with a concentrated hydrochloric acid solution, while cooling, and alkalized with a concentrated ammonium hydroxide solution. The product is extracted with trichloromethane. The extract is washed with water, dried, filtered and evaporated. The residue is crystallized from a mixture of 2,2'-oxybispropane and 2-propanol. The product is filtered off and dried, yielding 1,3-dihydro-1-(4-piperidinyl)-5-(trifluoromethyl)-2H-benzimidazol-2-one; mp. 198° C.

By repeating the procedure of Example I and using an equivalent amount of an appropriate substituted 2-nitro-chlorobenzene in place of the 4-chloro-α,α,α-trifluoro-3-nitrotoluene used therein, the following intermediates of formula (III) were obtained:

5,6-dichloro-1,3-dihydro-1-(4-piperidinyl)-2H-benzimidazol-2-one; mp. 250°–251.8° C.;

6-chloro-1,3-dihydro-1-(4-piperidinyl)-2H-benzimidazol-1-one; mp. 205° C.;

5-fluoro-1,3-dihydro-1-(4-piperidinyl)-2H-benzimidazol-2-one;

1,3-dihydro-5-methyl-1-(4-piperidinyl)-2H-benzimidazol-2-one;

6-chloro-1,3-dihydro-1-(4-piperidinyl)-5-(trifluoromethyl)-2H-benzimidazol-2-one; mp. 260° C.;

5-bromo-1,3-dihydro-1-(4-piperidinyl)-2H-benzimidazol-2-one; mp. 221.8° C.;

6-chloro-1,3-dihydro-7-methyl-1-(4-piperidinyl)-2H-benzimidazol-2-one; mp. 229.6° C.;

7-chloro-1,3-dihydro-1-(4-piperidinyl)-2H-benzimidazol-2-one; mp. 268.4° C.; and 1,3-dihydro-5-iodo-1-(4-piperidinyl)-2H-benzimidazol-2-one; mp. 260° C.

EXAMPLE II

To a stirred mixture of 1.9 parts of sodium hydride dispersion 78% and 100 parts of hexamethylphosphoric triamide are added portionwise 16.2 parts of ethyl 4-(5-chloro-2-oxo-1-benzimidazolinyl)-1-piperidinecarboxylate (exothermic reaction: temperature rises to 40° C.). After stirring for one hour at room temperature, there are added dropwise 10.6 parts of iodomethane (temperature rises to 40° C). Upon completion, stirring is continued overnight at 60° C. The reaction mixture is cooled, poured onto ice-water and the product is extracted with methylbenzene. The extract is dried, filtered and evaporated. The oily residue is triturated in 2,2'-oxybispropane. The product is filtered off and dried, yielding ethyl 4-(5-chloro-1,3-dihydro-3-methyl-2-oxo-2H-benzimidazol-1-yl)-1-piperidinecarboxylate; mp. 121.9° C.

A mixture of 12.8 parts of ethyl 4-(5-chloro-1,3-dihydro-3-methyl-2-oxo-2H-benzimidazol-1-yl)-1-piperidinecarboxylate, 20 parts of potassium hydroxide, 128 parts of 2-propanol and 2.5 parts of water is stirred and refluxed overnight. The reaction mixture is cooled and evaporated. Water is added to the residue and the product is extracted with trichloromethane. The extract is dried, filtered and evaporated. The residue is triturated in 2,2'-oxybispropane. The product is filtered off and dried, yielding 5-chloro-1,3-dihydro-3-methyl-1-(4-piperidinyl)-2H-benzimidazol-2-one; mp. 200.9° C.

The procedure of Example II was repeated except that the iodomethane used therein was replaced by an equivalent amount of (bromomethyl)benzene to yield 5-chloro-1,3-dihydro-3-(phenylmethyl)-1-(4-piperidinyl)-2H-benzimidazol-2-one; mp. 128° C.

EXAMPLE III

To a stirred solution of 1.9 parts of sodium hydride dispersion 75% in 100 parts of hexamethylphosphoric triamide are added portionwise 16.2 parts of ethyl 4-(5-chloro-2-oxo-1-benzimidazolinyl)-1-piperidinecarboxylate (exothermic reaction: temperature rises to 40° C). After stirring for one hour at room temperature, there are added dropwise 8.9 parts of 3-bromo-2-propyne (exothermic reaction: temperature rises to about 40° C). Upon completion, stirring is continued overnight at 60° C. The reaction mixture is cooled, poured onto ice-water and the product is extracted with methylbenzene. The extract is dried, filtered and evaporated. The oily residue is triturated in 2,2'-oxybispropane. The solid product is filtered off and dried, yielding ethyl 4-[5-chloro-1,3-dihydro-2-oxo-3-(2-propynyl)-2H-benzimidazol-1-yl]-1-piperidine-carboxylate; mp. 126.1° C.

A mixture of 14 parts of ethyl 4-[5-chloro-1,3-dihydro-2-oxo-3-(2-propynyl)-2H-benzimidazol-1-yl]-1-piperidinecarboxylate, 20 parts of potassium hydroxide, 128 parts of 2-propanol and 2.5 parts of water is stirred and refluxed overnight. After cooling, the solvent is evaporated and water is added to the residue. The product is extracted with methylbenzene. The extract is dried, filtered and evaporated. The oily residue is converted into the hydrochloride salt in 2,2'-oxybispropane and 2-propanol. The salt is filtered off and crystallized from ethanol, yielding 5-chloro-1,3-dihydro-3-(2-oxopropyl)-1-(4-piperidinyl)-2H-benzimidazol-2-one hydrochloride.

EXAMPLE IV

A. To a stirred mixture of 85.6 parts of methyl 3-methyl-4-oxo-1-piperidinecarboxylate and 240 parts of methanol are added 54.6 parts of benzenemethanamine (exothermic reaction). After stirring for 5 minutes, there are added 0.2 parts of 4-methylbenzenesulfonic acid and the whole is hydrogenated at normal pressure and at normal temperature with 10 parts of palladium-on-charcoal catalyst 10%. After the calculated amount of hydrogen is taken up, (about 20 hours), the catalyst is filtered off and the filtrate is evaporated. The residue is distilled, yielding methyl 4-amino-3-methyl-1-piperidinecarboxylate; bp. 136°–140° C. (water-jet).

B. A mixture of 43 parts of methyl 4-amino-3-methyl-1-piperidinecarboxylate, 57.6 parts of 1,4-dichloro-2-nitrobenzene, 32 parts of sodium carbonate, 0.2 parts of potassium iodide and 160 parts of cyclohexanol is stirred and refluxed (160°–163° C) for 20 hours with water-separator. The reaction mixture is evaporated. Water is added and the product is extracted with methylbenzene. The extract is dried, filtered and evaporated. The residue is purified by column-chromatography over silicagel, using a mixture of trichloromethane and 5% of methanol as eluent. The pure fractions are collected and the eluent is evaporated. Methylbenzene is added to the oily residue and the whole is washed with a diluted hydrochloric acid solution. After filtration over hyflo, the layers are separated. The methylbenzene phase is treated with activated charcoal. The latter is filtered off and the filtrate is dried, filtered and evaporated, yielding methyl 4-(4-chloro-2-nitrophenylamino)-3-methyl-1-piperidinecarboxylate as an oily residue.

A mixture of 51 parts of methyl 4-(4-chloro-2nitrophenylamino)-3-methyl-1-piperidinecarboxylate, 270 parts of tetrahydrofuran and 96 parts of methanol is hydrogenated at normal pressure and at normal temperature with 15 parts of raney-nickel catalyst. After the calculated amount of hydrogen is taken up (6 hours), the catalyst is filtered off and the filtrate is evaporated. The oily residue is triturated in warm 2,2'-oxybispropane. After cooling, the product is filtered off, pulverized in a mortar and triturated again in 2,2'-oxybispropane. The product is filtered off and dried, yielding methyl 4-(2-amino-4-chlorophenylamino)-3-methyl-1-piperidinecarboxylate.

A mixture of 30 parts of methyl 4-(2-amino-4-chlorophenylamino)-3-methyl-1-piperidinecarboxylate and 10 parts of urea is stirred and heated at 160°–180° C (oil-bath) for 3h. 30. The reaction mixture is cooled and the product is extracted with methylbenzene. The extract is washed successively with water, with a diluted hydrochloric acid solution and again with water, dried, filtered and evaporated. The oily residue is crystallized from a warm mixture of 2,2'-oxybispropane and a small amount of 2-propanol. After cooling, the product is filtered off and dried, yielding methyl 4-(5-chloro-1,3-dihydro-2-oxo-2H-benzimidazol-1-yl)-3-methyl-1-piperidinecarboxylate; mp. 196.2° C.

A mixture of 26 parts of methyl 4-(5-chloro-1,3-dihydro-2-oxo-2H-benzimidazol-1-yl)-3-methyl-1-piperidinecarboxylate, 36 parts of potassium hydroxide, 200 parts of 2-propanol and 6 parts of water is stirred and refluxed for 18 hours. The reaction mixture is evaporated and water is added to the residue. The whole is acidified with a concentrated hydrochloric acid solution, while cooling. The free base is liberated in the conventional manner and stirred with trichloromethane for 30 minutes. The layers are separated and the aqueous layer is extracted with trichloromethane. The combined organic phases are dried, filtered and evaporated. The oily residue solidifies on triturating in a mixture of 2,2'-oxybispropane and a small amount of 2-propanol. The product is filtered off and crystallized from 4-methyl-2-pentanone, yielding 5-chloro-1,3-dihydro-1-(3-methyl-4-piperidinyl)-2H-benzimidazol-2-one; mp. 198.9° C.

EXAMPLE V

A. To a stirred and refluxing mixture of 403 parts of ethyl 3-[(phenylmethyl)amino]butanoate and 160 parts of ethanol are added dropwise 100 parts of ethyl 2-propenoate. After stirring overnight at reflux temperature, a second portion of 100 parts of ethyl 2-propenoate is added dropwise. Upon completion, stirring is continued at reflux for 48 hours. The reaction mixture is evaporated, yielding a mixture of ethyl N-[2-(ethoxycarbonyl)-1-methylethyl]-N-(phenylmethyl)-β-alanine and ethyl N-[2-(ethoxycarbonyl)ethyl]-N-(phenylmethyl)-β-alanine as an oily residue. The latter is stirred at room temperature together with 17 parts of sodium carbonate in 900 parts of trichloromethane. Then there are added dropwise 217 parts of ethyl chloroformate. Upon completion, stirring is continued overnight. The mixture is washed with water, dried, filtered and evaporated. The residue is extracted with a diluted hydrochloric acid solution. The aqueous acid phase is washed with 2,2'-oxybispropane. The free base is liberated with ammonium hydroxide and extracted with 2,2'-oxybispropane. The extract is washed with water, dried, filtered and evaporated, yielding ethyl N-[2-(ethoxycarbonyl)-1-methylethyl]-N-(phenylmethyl)-β-alanine as a residue.

A mixture of 192.8 parts of ethyl N-[2(ethoxycarbonyl)-ethyl]-N-(phenylmethyl)-β-alanine and 280 parts of absolute ethanol is stirred in an hydrogenation vessel. Then there are added 45 parts of hydrochloric acid solution. After cooling, 10 parts of palladium-on-charcoal catalyst 5% are added and the whole is shaken at room temperature while one equivalent of hydrogen is taken up. The catalyst is filtered off and the filtrate is evaporated, yielding ethyl N-[2-(ethoxycarbonyl)ethyl]-β-alanine hydrochloride as an oily residue.

To a stirred solution of 150 parts of ethyl N-[2-(ethoxycarbonyl)ethyl]-β-alanine hydrochloride in 1800 parts of trichloromethane are added 150 parts of N,N-diethylethanamine, while cooling. Then there are added dropwise 68 parts of methyl chloroformate. Upon completion, stirring is continued overnight at room temperature. The formed precipitate is filtered off and the filter-cake is washed with methylbenzene. The filtrate is evaporated and water is added to the residue. The product is extracted with methylbenzene. The extract is washed three times with water, dried, filtered and evaporated. The residue is distilled, yielding ethyl N-[2-(ethoxycarbonyl)ethyl]-N-(methoxycarbonyl)-β-alanine; bp. 137°–140° C at 0.2 mm. pressure.

100 parts of sodium methoxide solution 30% in methanol are stirred and heated in 117 parts of dimethylbenzene. Methanol is distilled off, while there is added dropwise a solution of 111 parts of ethyl N-[2-(ethoxycarbonyl)-1-methylethyl]-N-(methoxycarbonyl)-β-alanine in 90 parts of dimethylbenzene. Upon completion, the methanol is further distilled off. The reaction mixture is cooled and decomposed by the addition of a mixture of glacial acetic acid and water (1 : 1 by volume). The aqueous acid phase is extracted twice with dimethylbenzene. The combined extracts are dried, filtered and evaporated, yielding ethyl 1-(methoxycarbonyl)-2-methyl-4-oxo-3-piperidinecarboxylate as an oily residue.

76 parts of ethyl 1-(methoxycarbonyl)-2-methyl-4-oxo-3-piperidinecarboxylate are hydrolyzed with 600 parts of ethanedioic acid solution 14% in water and the whole is stirred and refluxed for 40 hours. The product is extracted with trichloromethane. The extract is dried, filtered and evaporated. The residue is distilled, yielding methyl 2-methyl-4-oxo-1-piperidinecarboxylate; bp. 96°–99° C. at 0.2-9.3 mm. pressure.

A mixture of 56 parts of methyl 2-methyl-4-oxo-1-piperidinecarboxylate 35.4 parts of benzenemethanamine, 0.1 parts of 4-methylbenzenesulfonic acid and 240 parts of ethanol is stirred for 15 minutes at room temperature. The whole is hydrogenated at normal pressure and at room temperature with 7 parts of palladium-on-charcoal catalyst 10%. After the calculated amount of hydrogen is taken up, the catalyst is filtered off and the filtrate is evaporated. The residue is distilled, yielding methyl 4-amino-2-methyl-1-piperidine carboxylate; bp. 99°–102° C. at 0.2 mm. pressure.

B. A mixture of 44 parts of methyl 4-amino-2-methyl-1-piperidinecarboxylate, 57.6 parts of 1,4-dichloro-2-nitrobenzene, 32 parts of sodium carbonate, 0.2 parts of potassium iodide and 160 parts of cyclohexanol is stirred for 10 hours at 160° C. After cooling, the reaction mixture is evaporated and water is added to the residue. The product is extracted with methylbenzene. The extract is washed successively twice with water and twice with a diluted hydrochloric acid solution. The formed precipitate is filtered off over hyflo. The filtrate is washed twice with water, dried, filtered and evaporated. The residue is stirred in 2,2'-oxybispropane with activated charcoal. The latter is filtered off and the clear filtrate is evaporated. The oily residue is purified by column-chromatography over silicagel, using trichloromethane as eluent. The pure fractions are collected and the eluent is evaporated, yielding methyl 4-(4-chloro-2-nitrophenylamino)-2-methyl-1-piperidinecarboxylate as an oily residue.

A mixture of 39.6 parts of methyl 4-(4-chloro-2-nitrophenylamino)-2-methyl-1-piperidinecarboxylate and 450 parts of tetrahydrofuran is hydrogenated at 40 lbs./sq. inch and at room temperature with 2 parts of raney-nickel catalyst. After the calculated amount of hydrogen is taken up, the catalyst is filtered off. The filtrate is evaporated, yielding methyl 4-(2-amino-4-chlorophenylamino)-2-methyl-1-piperidinecarboxylate as an oily residue.

A mixture of 36 parts of methyl 4-(2-amino-4-chlorophenylamino)-2-methyl-1-piperidinecarboxylate and 14 parts of urea is stirred and heated in an oil-bath at 160° C. for 4 hours. After cooling, the reaction mixture is disslved in methylbenzene. The solution is washed successively three times with water, twice with a diluted hydrochloric acid solution and again three times with water, dried, filtered and evaporated. The oily residue is purified by column-chromatography over silicagel, using trichloromethane as eluent. The pure fractions are collected and the eluent is evaporated, yielding methyl 4-(5-chloro-1,3-dihydro-2-oxo-2H-benzimidazol-1-yl)-2-methyl-1-piperidinecarboxylate as an oily residue.

A mixture of 20 parts of methyl 4-(5-chloro-1,3-dihydro-2-oxo-2H-benzimidazol-1-yl)-2-methyl-1-piperidinecarboxylate, 20 parts of potassium hydroxide, 160 parts of 2-propanol and 3 parts of water is stirred and refluxed for 36 hours. The reaction mixture is evaporated and water is added to the residue. The whole is acidified with a hydrochloric acid solution. Then it is basified with ammonium hydroxide and the free base is extracted with trichloromethane. The extract is dried, filtered and evaporated. The residue is converted into the hydrochloride salt in 2-propanol. The salt is filtered off and dried, yielding 5-chloro-1,3- dihydro-1-(2-methyl-4-piperidinyl)-2H-benzimidazol-2-one hydrochloride.

EXAMPLE VI

By repeating the procedure of Example (IV-B) and using an equivalent amount of 4-chloro-α,α,α-trifluoro-3-nitrotoluene or 1,5-dichloro-4-(trifluoromethyl)-2-nitrobenzene in place of the 1,4-dichloro-2-nitrobenzene used therein, the following compounds are obtained respectively:

1,3-dihydro-1-(3-methyl-4-piperidinyl)-5-(trifluoromethyl)-2H-benzimidazol-2-one; and 6-chloro-1,3-dihydro-1-(3-methyl-4-piperidinyl)-5-(trifluoromethyl)-2H-benzimidazol-2-one.

EXAMPLE VII

When the procedure of Example (V-B) is repeated, except that the 1,4-dichloro-2-nitrobenzene used therein is replaced by an equivalent amount of 4-chloro-α,α,α-trifluoro-3-nitrotoluene or 1,5-dichloro-4-(trifluoromethyl)-2-nitrobenzene, the following compounds are obtained:

1,3-dihydro-1-(2-methyl-4-piperidinyl)-5-(trifluoromethyl)-2H-benzimidazol-2-one; and 6-chloro-1,3-dihydro-1-(2-methyl-4-piperidinyl)-5-(trifluoromethyl)-2H-benzimidazol-2-one.

B. PREPARATION OF FORMULA (I) FINAL PRODUCTS

EXAMPLE VIII

A mixture of 5 parts of 1-chloro-4,4-bis(p-fluorophenyl-butane 3.8 parts of 5-chloro-1-(4-piperidyl)-2-benzimidazolinone, 1.4 parts of sodium bicarbonate and 80 parts of absolute ethanol is stirred and refluxed for 24 hours. The reaction mixture is evaporated. Water and toluene are added to the residue and the whole is shaken vigorously. The layers are separated and the toluene layer is dried, filtered and evaporated. The oily residue is purified by column-chromatography over silicagel, using a mixture of chloroform and 5% of methanol as eluent. The pure fractions are collected and the eluent is evaporated. The oily residue is triturated in diisopropylether. The solid product is filtered off and crystallized from 4-methyl-2-pentanone, yielding 5-chloro-1 1-[4,4-bis(p-fluorophenyl)butyl]-4-piperidyl -2-benzimidazolinone; mp. 185.8° C.

EXAMPLE IX

A mixture of 7 parts of 1-chloro-4,4-bis(4-fluorophenyl)-butane, 5.75 parts of 5,6-dichloro-1,3-dihydro-1-(4-piperidinyl)-2H-benzimidazol-2-one, 8 parts of sodium carbonate and 100 parts of 4-methyl-2-pentanone is stirred and refluxed for 12 hours with water-separator. The reaction mixture is cooled to room temperature and water is added. The organic layer is separated, dried, filtered and evaporated. The oily residue is purified by column-chromatography over silicagel, using a mixture of trichloromethane and 10% of methanol as eluent. The pure fractions are collected and the eluent is evaporated. The solid residue is crystallized successively: once from 4-methyl-2-pentanone and twice from 2-propanol, yielding 5,6-dichloro-1{1-[4,4-bis(4-fluorophenyl)butyl]-4-piperidinyl}-1,3-dihydro-2H-benzimidazol-2-one 2-propanolate; mp. 182.5–184.2° C.

EXAMPLE X

A mixture of 5.7 parts of 1,3-dihydro-1-(4-piperidinyl)-5-(trifluoromethyl)-2H-benzimidazol-2-one, 6.4 parts of sodium carbonate, 0.2 parts of potassium iodide and 200 parts of 4-methyl-2-pentanone is distilled azeotropically for one hour. After cooling, 7 parts of 1-chloro-4,4-bis(4-fluorophenyl)butane are added and the whole is stirred and refluxed overnight. The reaction mixture is cooled, water is added and the layers are separated. The organic layer is dried, filtered and evaporated. The residue is crystallized from 2-propanol. The product is filtered off and dried, yielding 1-{1-[4,4-fluorophenyl)butyl]-4-piperidinyl}-1,3-dihydro-5-(trifluoromethylphenyl)-2H-benzimidazol-2-one; mp. 189.9° C.

EXAMPLE XI

A mixture of 5 parts of 6-chloro-1,3-dihydro-1-(4-piperidinyl)- 2H-benzimidazol-2-one, 6.4 parts of sodium carbonate, 0.2 parts of potassium iodide and 200 parts of 4-methyl-2-pentanone is stirred and refluxed for 30 minutes with water-separator. After cooling for awhile, there are added 7 parts of 1-chloro-4,4-bis(4-fluorophenyl)-butane and stirring at reflux is continued for 20 hours. The reaction mixture is cooled, water is added and the layers are separated. The organic layer is dried, filtered and evaporated. The oily residue is acidified with a diluted hydrochloric acid solution. After shaking thoroughly with toluene, the latter is decanted and discarded. The aqueous acid phase, together with the residual oil, is alkalized with ammonium hydroxide and the product is extracted with toluene. The extract is dried, filtered and evaporated. The oily residue is crystallized from 2-propanol, yielding 6-chloro-1{1-[4,4-bis(4-fluorophenyl)butyl]-4-piperidinyl}-1,3-dihydro-2H-benzimidazol-2-one 2-propanolate; mp. 174.6° C.

EXAMPLE XII

A mixture of 2.35 parts of 5-fluoro-1,3-dihydro-1-(4-piperidinyl)-2H-benzimidazol-2-one, 4.3 parts of sodium carbonate, 0.2 parts of potassium iodide and 160 parts of 4-methyl-2-pentanone is distilled azeotropically for one hour. After cooling, there are added 4.5 parts of 1-chloro-4,4-bis(4-fluorophenyl)butane and the whole is stirred for 24 hours at reflux. The reaction mixture is cooled, water is added and the layers are separated. The organic layer is washed with water, dried, filtered and evaporated. The residue is crystallized from 2-propanol. The product is filtered off and dried, yielding 5-fluoro-1-{1-[4,4-bis(4-fluorophenyl)-butyl]-4-piperidinyl}-1,3-dihydro-2H-benzimidazol-2-one; mp. 201.4° C.

EXAMPLE XIII

A mixture of 7 parts of 1-chloro-4,4-bis(4-fluorophenyl)-butane, 5.9 parts of 5-bromo-1,3-dihydro-1-(4-piperidinyl)-2H-benzimidazol-2-one, 6.4 parts of sodium carbonate, 0.2 parts of potassium iodide and 200 parts of 4-methyl-2-pentanone is stirred and refluxed overnight. The reaction mixture is cooled, water is added and the layers are separated. The organic phase is dried, filtered and evaporated. The residue is crystallized twice: first from a mixture of 2-propanol and 2,2'-oxybispropane and then from ethanol. The product is filtered off and dried, yielding 5-bromo-1-

{1- 4,4-bis(4-fluorophenyl)butyl]-4-piperidinyl}-1,3-dihydro-2H-benzimidazol-2-one; mp. 182° C.

EXAMPLE XIV

A mixture of 7 parts of 1-chloro-4,4-bis(4-fluorophenyl)-butane, 6.84 parts of 1,3-dihydro-5-iodo-1-(4-piperidinyl)-2H-benzimidazol-2-one, 6.4 parts of sodium carbonate, 0.2 parts of potassium iodide and 200 parts of 4-methyl-2-pentanone is stirred and refluxed for 24 hours with water-separator. After cooling, water is added and the layers are separated. The organic phase is dried, filtered and evaporated. The residue is purified by column-chromatography over silicagel, using a mixture of trichloromethane and 5% of methanol as eluent. The pure fractions are collected and the eluent is evaporated. The residue is crystallized from a mixture of 2,2'-oxybispropane and 2-propanol, yielding 1- 1-[4,4-bis(4-fluorophenyl)-butyl]-4-piperidinyl - 1,3-dihydro-5-iodo-2H-benzimidazol-2-one; mp. 179.3° C.

EXAMPLE XV

A mixture of 7.4 parts of 1,1-bis(-4-fluorophenyl)-4-iodobutane, 5 parts of 7-chloro-1,3-dihydro-1-(4-piperidinyl)-2H-benzimidazol-2-one, 5 parts of sodium carbonate and 56 parts of 4-methyl-2-pentanone is stirred and refluxed overnight. After cooling, the reaction mixture is poured onto water. The organic layer is separated, dried, filtered and concentrated to half its volume. From the residue, the product is allowed to crystallize. The product is filtered off and recrystallized from a mixture of 4-methyl-2-pentanone and 2-propanol, yielding 7-chloro-1-{1-[4,4-bis(4-fluorophenyl)butyl]-4-piperidinyl}-1,3-dihydro-2H-benzimidazol-2-one; mp. 215.4° C.

EXAMPLE XVI

A mixture of 7.6 parts of 1-chloro-4,4-bis(4-fluorophenyl)butane, 4.6 parts of 1,3-dihydro-5-methyl-1-(4-piperidinyl)-2H-benzimidazol-2-one, 10 parts of sodium carbonate, 0.1 parts of potassium iodide and 80 parts of 4-methyl-2-pentanone is stirred and refluxed overnight. The reaction mixture is cooled and poured onto water, whereupon the product is precipitated. It is filtered off, boiled in 2-propanol and treated with activated charcoal. The latter is filtered off and the product is allowed to crystallize from the filtrate, yielding 1-{1-[4,4-bis(4-fluorophenyl)butyl]-4-piperidinyl}-1,3-dihydro-5-methyl-2H-benzimidazol-2-one 2-propanolate; mp. 190 ° C.

EXAMPLE XVII

A mixture of 3.5 parts of 1-chloro-4,4-bis(4-fluorophenyl)-butane, 2.5 parts of 6-chloro-1,3-dihydro-1-(4-piperidinyl)-5-(trifluoromethyl)-2H-benzimidazol-2-one, 2.65 parts of sodium carbonate and 100 parts of 4-methyl-2-pentanone is stirred and refluxed overnight with water-separator. The reaction mixture is cooled to room temperature and water is added. The organic layer is separated, dried, filtered and evaporated. The solid residue is purified by column-chromatography over silicagel, using a mixture of trichloromethane and 5% of methanol as eluent. The pure fractions are collected and the eluent is evaporated. The residue is crystallized from 2-propanol, yielding 6-chloro-1-{1-[4,4-bis(4-fluorophenyl)butyl]-4-piperidinyl}-1,3-dihydro-5-(trifluoromethyl)-2H-benzimidazol-2-one 2-propanolate; mp. 200° C.

EXAMPLE XVIII

A mixture of 3.5 parts of 1,1-bis(4-fluorophenyl)-4-chlorobutane, 3.65 parts of 6-chloro-1,3-dihydro-7-methyl-1-(4-piperidinyl)-2H-benzimidazol-2-one, 2.65 parts of sodium carbonate, 0.1 parts of potassium iodide and 100 parts of 4-methyl-2-pentanone is stirred and refluxed for 36 hours. After cooling to room temperature, water is added and the layers are separated. The organic phase is dried, filtered and evaporated. The residue is converted into the hydrochloride salt in methylbenzene. The aqueous- and methylbenzene phases are decanted and discarded. From the sticky residual salt, the free base is liberated in the conventional manner and extracted with trichloromethane. The extract is dried, filtered and evaporated. The residue is crystallized from 4-methyl-2-pentanone, yielding 6-chloro-1-{1-[4,4-bis(4-fluorophenyl)butyl]-4-piperidinyl}-1,3-dihydro-7-methyl-2H-benzimidazol-2-one; mp. 171.9° C.

EXAMPLE XIX

A mixture of 4.7 parts of 4-chloro-1,1'-butylidene bis[4-chlorobenzene], 3 parts of 5-chloro-1-(4-piperidyl)-2-benzimidazolinone, 3.7 parts of sodium carbonate and 100 parts of 4-methyl-2-pentanone is stirred and refluxed overnight with water-separator. The reaction mixture is cooled, water is added and the layers are separated. The organic layer is dried, filtered and evaporated. The residue is purified by column-chromatography over silicagel, using a mixture of trichloromethane and 5% of methanol as eluent. The pure fractions are collected and the eluent is evaporated. The residue is crystallized from a mixture of 2-propanol and 2,2'-oxybispropane, yielding 5-chloro-1-{1-[4,4-bis(4-chlorophenyl)butyl]-4-piperidinyl}-1,3-dihydro-2H-benzimidazol-2-one; mp. 165.4° C.

EXAMPLE XX

A mixture of 7.35 parts of 1-chloro-4,4-diphenylbutane, 6.3 parts of 5-chloro-1-(4-piperidyl)-2-benzimidazolinone, 6.35 parts of sodium carbonate, 0.1 parts of potassium iodide and 200 parts of 4-methyl-2-pentanone is stirred and refluxed for 48 hours with water-separator. The reaction mixture is cooled to room temperature and water is added. The organic layer is separated, dried, filtered and evaporated. The residue is crystallized twice; first from 2-propanol and then from 4-methyl-2-pentanone, yielding 5-chloro-1,3-dihydro-1-[1-(4,4-diphenylbutyl)-4-piperidinyl]-2-H-benzimidazol-2-one; mp. 164.7° C.

EXAMPLE XXI

A mixture of 7.85 parts of 1-chloro-4-(4-fluorophenyl)-4-phenylbutane, 6.3 parts of 5-chloro-1-(4-piperidyl)-2-benzimidazolinone, 6.35 parts of sodium carbonate, 0.1 parts of potassium iodide and 200 parts of 4-methyl-2-pentanone is stirred and refluxed for 48 hours with water-separator. The reaction mixture is cooled to room temperature and water is added. The organic layer is separated, dried, filtered and evaporated. The residue is crystallized from 4-methyl-2-pentanone, yielding 5-chloro-1-{1-[4-(4-fluorophenyl)-4-phenyl-butyl]-4-piperidinyl}-1,3-dihydro-2H-benzimidazol-2-one; mp. 182.9° C.

EXAMPLE XXII

A mixture of 9.35 parts of 1-chloro-4-phenyl-4-(3-trifluoromethylphenyl)butane, 6.3 parts of 5-chloro-1-(4-piperidyl)-2-benzimidazolinone, 6.35 parts of sodium carbonate, 0.1 parts of potassium iodide and 200 parts of 4-methyl-2-pentanone is stirred and refluxed overnight with water-separator. After cooling to room temperature, water is added and the layers are separated. The organic phase is dried, filtered and evaporated. The oily residue is purified by column-chromatography over silicagel, using a mixture of trichloromethane and 5% of methanol as eluent. The pure fractions are collected and the eluent is evaporated. The residue is crystallized from 4-methyl-2-pentanone, yielding 5-chloro-1,3-dihydro-1-[1-{4-phenyl-4-[3-(trifluoromethyl)phenyl]butyl} 4-piperidinyl]-2H-benzimidazol-2-one hydrate; mp. 114.9° C.

EXAMPLE XXIII

A mixture of 7 parts of 1-chloro-4,4-bis(4-fluorophenyl)-butane, 5.5 parts of 5-chloro-1,3-dihydro-1-(2-methyl-4-piperidinyl)-2H-benzimidazol-2-one, 6.4 parts of sodium carbonate, 0.2 parts of potassium iodide and 160 parts of 4-methyl-2-pentanone is stirred and refluxed for 36 hours. After cooling, water is added and the layers are separated. The organic phase is dried, filtered and evaporated. The oily residue is converted into the hydrochloride salt in 2-propanol and 2,2'-oxybispropane. The salt is filtered off. The free base is liberated in the conventional manner and extracted with methylbenzene. The extract is dried, filtered and evaporated. The residue is purified by column-chromatography over silicagel, using a mixture of trichloromethane and 5% of methanol as eluent. The pure fractions are collected and the eluent is evaporated. The oily residue is crystallized from 2-propanol, yielding 5-chloro-1-{1-[4,4-bis(4-fluorophenyl)butyl]-2-methyl-4-piperidinyl}-1,3-dihydro-2H-benzimidazol-2-one; mp. 171.1° C.

EXAMPLE XXIV

A mixture of 5.3 parts of 5-chloro-1,3-dihydro-1-(3-methyl-4-piperidinyl)-2H-benzimidazol-2-one, 6.4 parts of sodium carbonate, 0.2 parts of potassium iodide and 200 parts of 4-methyl-2-pentanone is stirred and refluxed for 30 minutes with water-separator. After cooling, there are added 7 parts of 1-chloro-4,4-bis(4-fluorophenyl)butane and stirring at reflux temperature is continued for 18 hours. The reaction mixture is cooled, water is added and the layers are separated. The organic phase is dried, filtered and evaporated. Methylbenzene is added to the oily residue and the whole is acidified with a diluted hydrochloric acid solution. After shaking thoroughly, the methylbenzene-phase is decanted and discarded. The aqueous acid phase, together with the residual oil, is alkalized with ammonium hydroxide and the product is extracted again with methylbenzene. The extract is dried, filtered and evaporated. The residue is purified by column-chromatography over silicagel, using a mixture of trichloromethane and 5% of methanol as eluent. The pure fractions are collected and the eluent is evaporated. The residue is crystallized from a mixture of 2,2'-oxybispropane and a small amount of 2-propanol, yielding 5-chloro-1-{1-[4,4-bis(4-fluorophenyl)butyl]-3-methyl-4-piperidinyl}-1,3-dihydro-2H-benzimidazol-2-one; mp. 141.7° C.

EXAMPLE XXV

To a stirred mixture of 8.8 parts of 5-chloro-1-{1-[4,4-bis(p-fluorophenyl)butyl]-4-piperidyl}-2-benzimidazolinone, 1 part of N,N,N-trimethylbenzenemethanaminimum hydroxide solution 40% in methanol and 135 parts of tetrahydrofuran is added dropwise a solution of 8.6 parts of methyl 2-propenoate in 45 parts of tetrahydrofuran at 45° C. Upon completion, stirring is continued overnight at 50° C. The reaction mixture is evaporated. Water is added to the residue and the product is extracted with methylbenzene. The extract is dried, filtered and evaporated. The oily residue is purified by column-chromatography over silicagel, using a mixture of trichloromethane and 5% of methanol as eluent. The pure fractions are collected and the eluent is evaporated. The oily residue is crystallized from a mixture of 2,2'-oxybispropane and 2-propanol, yielding methyl 6-chloro-3-{1-[4,4-bis(4-fluorophenyl)butyl]-4-piperidinyl}-1,3-dihydro-2-oxo-2H-benzimidazole 1-propanoate; mp. 186.2° C.

EXAMPLE XXVI

A mixture of 7 parts of 1-chloro-4,4-bis(4-fluorophenyl)-butane, 5 parts of 5-chloro-1,3-dihydro-3-(2-oxopropyl)-1-(4-piperidinyl)-2H-benzimidazol-2-one, 6.4 parts of sodium carbonate, 0.2 parts of potassium iodide and 160 parts of 4-methyl-2-pentanone is stirred and refluxed for 24 hours. After cooling, water is added and the layers are separated. The organic phase is dried, filtered and evaporated. The oily residue is stirred while warming in 2,2'-oxybispropane. The turbid mixture is filtered hot over hyflo and the clear filtrate is allowed to cool to room temperature while stirring. The crystallized product is filtered off and recrystallized from 2-propanol, yielding 5-chloro-1-{1-[4,4-bis(4-fluorophenyl)butyl]-4-piperidinyl}-1,3-dihydro-3-(2-oxopropyl)-2H-benzimidazol-2-one; mp. 175.3° C.

EXAMPLE XXVII

A mixture of 6.8 parts of 5-chloro-1,3-dihydro-3-(phenylmethyl)-1-(4-piperidinyl)-2H-benzimidazol-2-one, 6.4 parts of sodium carbonate, 0.1 parts of potassium iodide and 200 parts of 4-methyl-2-pentanone is stirred and refluxed for 30 minutes with water-separator. After cooling, 7 parts of 1-chloro-4,4-bis(4-fluorophenyl)butane are added and stirring at reflux temperature is continued overnight. The reaction mixture is cooled, water is added and the layers are separated. The organic phase is dried, filtered and evaporated. The oily residue is crystallized twice: first from 2,2'-oxybispropane and then from 2-propanol, yielding 5-chloro-1-{1-[4,4-bis(4-fluorophenyl)butyl]-4-piperidinyl}-1,3-dihydro-3-(phenylmethyl)-2H-benzimidazol-2-one; mp. 141.5° C.

EXAMPLE XXVIII

A mixture of 5,3 parts of 5-chloro-1,3-dihydro-3-methyl-1-(4-piperidinyl)-2H-benzimidazol-2-one, 6.4 parts of sodium carbonate, 0.2 parts of potassium iodide and 200 parts of 4-methyl-2-pentanone is stirred and refluxed for 30 minutes with water-separator. After cooling, there are added 7 parts of 1-chloro-4,4-bis(4-fluorophenyl)-butane and stirring at reflux temperature is continued overnight. The reaction mixture is cooled, water is added and the layers are separated. The organic phase is dried, filtered and evaporated. The oily residue is triturated in 2,2'-oxybispropane. The product is filtered off, dried and crystallized from 2-propanol, yielding 5-chloro-1-{1-[4,4-bis(4-fluorophenyl)butyl]-4-piperidinyl}-1,3-dihydro-3-methyl-2H-benzimidazol-2-one; mp. 155.8° C.

EXAMPLE XXIX

When the procedure of Example VIII is repeated, except that the 5-chloro-1-(4-piperidyl)-2-benzimidazolinone used therein is replaced by an equivalent amount of an appropriately substituted intermediate of formula (III), the following compounds of formula (I) are obtained.

1-{1-[4,4-bis(4-fluorophenyl)butyl]-3-methyl-4-piperidinyl}-1,3-dihydro-5-(trifluoromethyl)-2H-benzimidazol-2-one;

6-chloro-1-{1-[4,4-bis(4-fluorophenyl)butyl]-3-methyl-4-piperidinyl}-1,3-dihydro-5-(trifluoromethyl)-2H-benzimidazol-2-one;

1-{1-[4,4-bis(4-fluorophenyl)butyl]-2-methyl-4-piperidinyl}-1,3-dihydro-5-(trifluoromethyl)-2H-benzimidazol-2-one;

6-chloro-1-{1-[4,4-bis(4-fluorophenyl)butyl -2-methyl 4-piperidinyl}-1,3-dihydro-5-(trifluoromethyl)-2H-benzimidazol-2-one;

5-bromo-1-{1-[4,4-bis(4-fluorophenyl)butyl]-3-methyl-4-piperidinyl}-1,3-dihydro-2H-benzimidazol-2-one;

5-bromo-1-{1-[4,4-bis(4-fluorophenyl)butyl]-2-methyl-4-piperidinyl}-1,3-dihydro-2H-benzimidazol-2-one;

5,6-dichloro-1-{1-[4,4-bis(4-fluorophenyl)butyl]-3-methyl-4-piperidinyl }-1,3-dihydro-2H-benzimidazol-2-one; and 5,6-dichloro-1-{1-[4,4-bis(4-fluorophenyl)butyl]-2-methyl-4-piperidinyl}-1,3-dihydro-2H-benzimidazol-2-one.

EXAMPLE XXX

The procedure of Example XXV may be employed to prepare the following compounds of formula (I) wherein L stands for a loweralkoxycarbonylethyl chain:

methyl 5,6-dichloro-1-{1-[4,4-bis(4-fluorophenyl)butyl]-4-piperidinyl}-1,3-dihydro-2-oxo-2H-benzimidazole-2-propanoate;

methyl 5-chloro-1-{1-[4,4-bis(4-fluorophenyl)butyl]-3-methyl-4-piperidinyl}-1,3-dihydro-2-oxo-2H-benzimidazole-2-propanoate;

methyl 5-bromo-1-{1-[4,4-bis(4-fluorophenyl)butyl]-4-piperidinyl}-1,3-dihydro-2-oxo-2H-benzimidazole-2-propanoate;

methyl 6-chloro-1-{1-[4,4-bis(4-fluorophenyl)butyl]-4-piperidinyl}-1,3-dihydro-2-oxo-2H-benzimidazole-2-propanoate;

ethyl 5,6-dichloro-1-{1-[4,4-bis(4-fluorophenyl)butyl]-4-pipepridinyl}-1,3-dihydro-2-oxo-2H-benzimidazole-2-propanoate;

ethyl 5-chloro-1-{1-[4,4-bis(4-fluorophenyl)butyl]-4-piperidinyl}-1,3-dihydro-2-oxo-2H-benzimidazole-2-propanoate; and ethyl 5-bromo-1-{1-[4,4-bis(4-fluorophenyl)butyl]-4-piperidinyl}-1,3-dihydro-2-oxo-2H-benzimidazole-2-propanoate.

We claim:

1. A compound selected from the group consisting of a benzimidazolinone derivative having the formula:

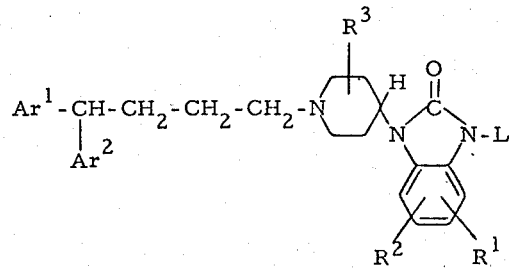

and the therapeutically acceptable acid addition salts thereof, wherein:

$Ar^1$ and $Ar^2$ are each a member independently selected from the group consisting of phenyl, halophenyl and trifluoromethylphenyl;

$R^1$ is a member selected from the group consisting of halo, loweralkyl and trifluoromethyl;

$R^2$ is a member selected from the group consisting of hydrogen, halo, loweralkyl and trifluoromethyl;

$R^3$ is a member selected from the group consisting of hydrogen and methyl, provided that, when said $R^3$ is methyl, then said $R^3$ is in the 2- or 3-position of the piperidine-nucleus; and L is a member selected from the group consisting of hydrogen, loweralkyl, loweralkyloxycarbonyl-loweralkyl, loweralkylcarbonyl-loweralkyl and phenyl-loweralkyl.

2. 5-Chloro-1-{1-[4,4-bis(p-fluorophenyl)butyl]-4-piperidyl}-2-benzimidazolinone.

3. 5,6-Dichloro-1-{1-[4,4-bis(4-fluorophenyl)butyl]-4-piperidinyl}-1,3-dihydro-2H-benzimidazol-2-one 2-propanolate.

4. 5-Chloro-1-{1-[4,4-bis(4-fluorophenyl)butyl]-3-methyl-4-piperidinyl}-1,3-dihydro-2H-benzimidazol-2-one.

5. 5-Bromo-1-{1-[4,4-bis(4-fluorophenyl)butyl]-4-piperidinyl}-1,3-dihydro-2H-benzimidazol-2-one.

6. Methyl 5-chloro-1-{1-[4,4-bis(4-fluorophenyl)butyl]-4-piperidinyl}-1,3-dihydro-2-oxo-2H-benzimidazole-2-propanoate.

* * * * *

UNITED STATES PATENT AND TRADEMARK OFFICE
CERTIFICATE OF CORRECTION

PATENT NO. : 3,989,707
DATED : November 2, 1976
INVENTOR(S) : Paul Adriaan Jan Janssen et al It is certified that error appears in the above-identified patent and that said Letters Patent are hereby corrected as shown below:

In Column 18, line 2, "0.2-9.3" should read --- 0.2-0.3 ---.

In Column 18, line 47, "disslved" should read --- dissolved ---.

In Column 19, line 65, "1-{1-8" should read --- 1-{1-[ ---.

In Column 20, line 14, "1-}1-[4,4-fluorophenyl)" should read --- 1-{1-[4,4-bis(4- fluorophenyl) --.

In Column 26, line 31, Claim 1, should read --- $R^1$ is halo; ---.

In Column 26, line 33, Claim 1, should read --- $R^2$ is a member selected from the group consisting of hydrogen and halo, ---.

Signed and Sealed this

Eleventh Day of July 1978

[SEAL]

Attest:

RUTH C. MASON
Attesting Officer

DONALD W. BANNER
Commissioner of Patents and Trademarks